United States Patent [19]

Fleminger et al.

[11] Patent Number: 5,104,931
[45] Date of Patent: Apr. 14, 1992

[54] PROCESS FOR THE PRODUCTION OF IMMOBILIZED ANTIBODIES

[75] Inventors: Gideon Fleminger, Rehovot; Tamar Wolf, Kfar-Saba; Eran Hadas, Rishon Letzion, all of Israel

[73] Assignee: Rohm GmbH Chemische Fabrik, Darmstadt, Fed. Rep. of Germany

[21] Appl. No.: 497,537

[22] Filed: Mar. 22, 1990

[30] Foreign Application Priority Data

Mar. 22, 1989 [DE] Fed. Rep. of Germany ....... 3909456

[51] Int. Cl.$^5$ .............................................. C08G 63/91
[52] U.S. Cl. .................................. 525/54.1; 435/177; 435/180; 530/402; 530/405; 530/810; 530/812; 530/817
[58] Field of Search .............. 530/402, 405, 812, 817, 530/810; 525/54.1; 435/177, 180

[56] References Cited

U.S. PATENT DOCUMENTS 4,948,836 8/1990 Solomon et al. .

FOREIGN PATENT DOCUMENTS 1571992 7/1980 United Kingdom .
2212500 7/1989 United Kingdom .

OTHER PUBLICATIONS

Gideon Fleminger et al, Oriented Immobilization of Periodate-Oxidized Monoclonal Antibodies on Amino and Hydrazide Derivatives of Eupergit C, *Applied Biochemistry and Biotechnology*, vol. 23, 1990, pp. 123-136.
Gideon Fleminger et al, Single Step Oxidative Binding of Antibodies to Hydrazide-Modified Eupergit C, *Applied Biochemistry and Biotechnology*, 1990, pp. 231-238.

*Primary Examiner*—Joseph L. Schofer
*Assistant Examiner*—Tom Weber
*Attorney, Agent, or Firm*—Oblon, Spivak, McClelland, Maier & Neustadt

[57] ABSTRACT

A single-step procedure for the immobilization of antibodies, comprising reacting a purified antibody with buffered periodate in an amount sufficient to produce aldehyde groups in the presence of a polymer carrier material which has been modified with adipic acid dihydrazide is disclosed. The present invention provides dramatic improvements in activity.

8 Claims, No Drawings

PROCESS FOR THE PRODUCTION OF IMMOBILIZED ANTIBODIES

BACKGROUND OF THE INVENTION

1. Field of the Invention

The present invention concerns an improved process for the production of immobilized antibodies, with regiospecific conjugates of antibodies containing oligosaccharides being formed by means of oxidative modification of the carbohydrate region of the antibodies.

2. Discussion of the Prior Art

The related U.S. Application Ser. No. 07/270,280 now U.S. Pat. No. 4,948,836 describes immobilized antibodies which are bound covalently to a matrix polymer, specifically by means of a modification in the carbohydrate region of the antibodies. Binding of the antibodies is achieved by a condensation reaction between at least one aldehyde group in the oxidatively modified carbohydrate region and at least one epoxide function of a matrix polymer. The polymer is modified by means of a bifunctional reagent which consists of a spacer with at least a three link chain and an end group suitable for condensation with the oxidatively produced aldehyde function of the antibody. A group at the other end of the bifunctional reagent reacts covalently with the epoxy group of the polymer.

Although the technique described in the aforementioned U.S. patent application results in very usable products, there continues to be significant interest in improving the process. For example, shortening the process period and simplifying the process itself has a positive effect on the overall result given the notorious sensitivity of antibodies. Therefore, the present invention is best understood as an improved process, based on the teaching of the U.S. Pat. No. 4,948,836.

The present process is based on oxidative binding of antibodies containing oligosaccharide moieties which have been oxidized by means of periodate, to a polymer carrier (ADH-PC) modified by means of adipic acid dihydrazide, in a single-crucible reaction.

In the multi-stage method which is disclosed in the aforementioned patent application the antibodies are first oxidized with periodate, then excess reagent is removed by treatment with ethylene glycol followed by gel filtration, concentration, and finally coupling of the antibodies to the hydrazide-modified polymer carrier. In contrast, in the present new process, the antibodies are oxidized to the aldehyde stage and then incubated with the polymer carrier ADH-PC which has been modified with adipic acid dihydrazide, in a single work step and without isolation or purification of intermediates. This process allows for efficient coupling of the sensitive antibody to the polymer without physical losses of material, nor losses in binding activity of the antibody.

The present invention therefore concerns a process for the production of immobilized antibodies containing oligosaccharide, by condensation of the antibodies present in oxidized form, with a carrier ADH-PC modified with adipic acid dihydrazide. The antibodies are incubated in a single-crucible process in an aqueous medium which simultaneously contains periodate (in amounts which are sufficient for oxidation to the aldehyde in the area of the carbohydrate region of the antibodies) and the polymer carrier material modified by means of adipic acid dihydrazide.

In this way an oxidative, covalent fixation is obtained since the aldehyde groups, once they have occurred due to oxidation, react directly with the adipic acid dihydrazide (ADH) groups of the carrier ADH-PC.

SUMMARY OF THE INVENTION

An object of the present invention is to provide a process for the immobilization of antibodies by a single-crucible reaction comprising a purified antibody using a buffered periodate solution to oxidize the carbohydrate region of the antibody while in the presence of a polymer carrier material which has been modified with adipic acid dihydrazide.

Another object of this invention is to provide a single-crucible reaction wherein the polymer is a copolymer of acrylamide or methacrylamide and glycidyl acrylate or glycidyl methacrylate which has been modified with adipic acid dihydrazide.

Another object is to provide an oxidation and coupling reaction process which can be completed in approximately 30–60 minutes.

Another object is to provide a rapid oxidation and coupling reaction process which may be conducted at approximately 4° C.

DETAILED DESCRIPTION OF THE INVENTION

The Polymer Carrier Material ADH-PC

For the present "single-crucible" process, polymers which do not contain any geminal hydroxyl groups are preferred. If a matrix material based on a carbohydrate, such as agarose or sepharose is used, the polymer is also subject to attack by periodate oxidation. Therefore, the matrix polymer (MP) of the present invention is preferably a cross-linked copolymerizate of acrylamide or methacrylamide and glycidyl acrylate or glycidyl methacrylate, which preferably consists of bead-shaped particles.

Such matrix polymerizates are described in DE-C 27 22 751, i.e. U.S. Pat. No. 4,190,713, as well as U.S. Pat. No. 4,511,694. The beads generally have a diameter of 5–1000 μm, especially 30–1000 μm, and have an interior cavity (hollow beads).

As a reference for the content of glycidyl groups in the matrix polymerizate MP which can be brought to reaction, a value of 0.8–2.5 μmol per mg dry carrier material is preferred.

Additional characteristics of a commercially available matrix polymerizate (EUPERGIT C from Rohm GmbH) which is representative of the preferred MP are evident from the following table.

| Characteristics | Dimension |
| --- | --- |
| average grain size: | 140–180 μm |
| pore diameter: | 40 nm |
| exclusion limit = $M_{LIM}$: | $2 \times 10^5$ Daltons |
| binding-active surface: | 180 m²/g (dry) |
| epoxide content: | 800–1000 mmol/g (dry) |
| water absorption: | 2.3 ml/g (dry) |
| density = $d_4^{20}$: | 1.20 |
| bulk density: | 0.34 g/ml |
| binding capacity: (under usual conditions) | |
| human albumin: | 48 mg/g (moist) |
| human IgG: | 34 mg/g (moist) |
| swelling behavior with regard to water: | 1:1.4 1 ml (dry) yields 1.4 ml (moist) |
| solubility (in water, buffers | insoluble |

| Characteristics | Dimension |
| --- | --- |
| or organic solvents): | |
| pressure stability: | 300 bar |

Under the electron microscope one can see the microporous structure of the beads with channels and cavities which have a diameter of 0.1 -2.5 μm (1,000 to 25,000 Å), so that enzyme or substrate molecules with a size of 10 -100 Å can reach the entire interior of the microporous matrix.

Production of the Polymer Carrier Material ADH-PC

In one embodiment of the present method a matrix polymerizate (MP) built up of (meth)acrylamide and glycidyl (meth)acrylate, preferably consisting of bead-shaped particles (see above), especially the product EUPERGIT C ® from the company Rohm GmbH, Darmstadt, is used.

The polymer is modified with a bifunctional reagent such as the commercially available adipic acid dihydrazide, in a suitable buffer solution in the alkaline range. For example a phosphate buffer at pH 8.8, for a certain period of time, for example 16 ±3 hours, at room temperature is suitable.

The bifunctional reagent is preferably used in amounts of 0.1 -10 mol per gram of polymer carrier MP, especially EUPERGIT C ®, dry weight, especially 1 μmol bifunctional reagent per gram dry weight. It is practical to wash the modified matrix polymerizate ADH-PC with phosphate standard buffer (PBS). It is preferably equilibrated with buffer (for example 0.1 M acetate buffer) at pH 5.5 and stored at a low temperature, for example at 4° C.

Implementation of the Invention

Purification of the Antibodies

The use of all antibodies are within the scope of the present invention since they are known to contain carbohydrate groups and are sufficiently stable with regard to chemical modification, i.e. periodate oxidation, and accessible to subsequent fixation. As a point of departure, a content of approximately 3% carbohydrate proportion can be assumed for the antibodies. Monoclonal antibodies are the focus of interest. Processes for the production of monoclonal antibodies are sufficiently known. [Cf. Kirk-Othmer, Encyclopedia of Chemical Technology, 3rd. ed., Vol. 23, J. Wiley (1983), pp. 637 to 643; D. Baron, U. Hartlaub, Humane Molekulare Antikorper [Human Molecular Antibodies], Gustav Fischer Verlag, Stuttgart, New York 1987].

In detail, the procedure can be as follows: The monoclonal antibodies, purified by various purification processes, such as ammonium sulfate precipitation, ion exchange chromatography and/or affinity chromatography, are preferably dialyzed before oxidation, for example with a suitable, compatible buffer, in the pH range around 5.5.

Anticarboxypeptidase antibodies (CPA9), for example, have been proven to be very suitable for use in the present process.

It is practical to partially purify the ascites liquor with an ammonium sulfate precipitation step (50% saturated solution, 16 hours at 4° C). Then it is taken up in ten times the volume of phosphate standard buffer (PBS) with a pH of 7.4 and dialyzed against PBS at 4° C. for 16 hours.

In some cases, antibodies purified by means of ammonium sulfate treatment are further purified with immobilized antigen in an EUPERGIT C column.

The Single-Crucible Process

The single-crucible process for fixation of the antibodies can generally be carried out using the polymer carriers ADH-PC and the antibodies described above. As in the state of the art, the risk of internal cross-linking of the antibodies is reduced or precluded by working at a relatively low pH, preferably in the range around 5.5.

The preferred method consists of using sodium periodate in 0.01–1.0 molar concentration, preferably 0.05 to 0.5 molar concentration, in a suitable inert buffer solution in a pH range of 3.0–7.0, preferably about 5.5. For example 0.1 M acetate buffer is suitable.

Conversion takes place at a relatively low temperature, approximately 0 -5° C., preferably at about 4° C., in the dark. The oxidation can be stopped, for example, by adding small amounts of ethylene glycol.

The process will be explained in more detail using the example of the anticarboxypeptidase antibody (CPA9). Binding of the CPA9 antibody to the carrier ADH-PC was studied with various periodate concentrations and with variations of the reaction time.

In a typical experiment, 5 mg ADH-modified EUPERGIT C as the carrier ADH-PC is mixed with 25 μg of the monoolonal antibody and 1 -10 mmol sodium periodate (final ooncentration) in 0.1 molar sodium buffer with a pH of 5.5. The mixture is stirred for 10 -120 min at 4° C., in the dark. After the reaction ends, the top fraction is separated and the antibody content of the top fraction is determined a) by means of ELISA Morcote and b) by means of protein determination.

After extensive washing of the carrier material with standard phosphate buffer PBS, the activity of the bound antibodies is determined using the Enzymatic Determination Method.

Enzymatic Determination Method of the Antigen Binding Activity of Antibodies Fixed on the Carrier ADH-PC The antibodies immobilized on the carrier material ADH-PC, for example ADH-modified EUPERGIT C, for example in batches of 1 -5 mg carrier material which carries 5 -25 μg antibodies, are incubated with an excess of antigen, such as anticarboxypeptidase (CPA) antibodies or anti-horseradish peroxidase (HRP) antibodies (>2 mol antigen per mole bound antibody) for 1 hour at room temperature. Non-bound antigen is then removed by extensive washing with PBS. The proportion of bound antigen is determined by means of enzymatic determination methods, in the following manner.

Determination of CPA Activity

A EUPERGIT C antibody-antigen complex (1 -5 ml; 4 -°μl) ) is mixed with hyppuryl-L-phenyl alanine (50 μl of a 10 mmol solution in PBS containing 0.5 mol NaCl) and the volume is filled up to 100 μl with PBS with a 0.5 molar content of NaCl. This mixture is incubated at room temperature for 10 minutes, while shaking. At the end of the incubation period, a sample (10 -50 μl) of the top fraction from the reaction mixture is placed into the depression of an ELISA microtiter plate and converted with ninhydrin reagent (3 % by weight ninhydrin in methyl cellosolve) as follows.

To each sample, 100 μl freshly prepared ninhydrin reagent and 50 μl of a freshly prepared solution of 0.2M sodium cyanide in 3.8 molar sodium acetate buffer, pH 5.3, are added. This mixture is heated to 95° C. for 20 minutes. Then a color determination of the blue coloration at 500 nm is made on the ELISA reader.

The correlation between the color development and the enzyme content is carried out using two types of calibration curves:

i) Using the ninhydrine determination values of a predetermined amount of phenyl alanine.

ii) From activity measurements of known amounts of the enzyme carboxypeptidase.

Determination of Horseradish Peroxidase

The EUPERGIT C antibody-antigen complex (0.1 –2.0 ng) is mixed with 1 ml of an o-phenylene diamine reagent (2 mg o-phenylenediamine in 1 ml of a 50 millimolar sodium citrate buffer at pH 5.0, which contains 0.08% by weight hydrogen peroxide). After 1 min, the reaction is stopped by adding 0.5 ml 5 normal HCl. 200 μl of the top fraction from the reaction are placed into an ELISA microtiter plate. Then the intensity of the coloration that has developed at 402 nm is determined by a reference measurement of the absorption at 405 nm, using an ELISA reader. With a standard curve that was obtained with known amounts of horseradish peroxidase, the correlation between the color development in the sample and its enzyme content can be determined.

Determination of the Immuno-Capacity of the Antibodies Fixed According to the Invention The binding capacity of the antibodies immobilized according to the invention is determined by measuring the antigens, particularly the enzymes such as anticarboxypeptidase (CPA), which bind to the antibodies. For this purpose, CPA, for example, in the same quantities, is added to beakers which each contain 100 mg of the polymer carrier material ADH-PC but with different charges of immobilized monoclonal antibodies. The proportion of CPA bound to the antibodies of the polymer matrix was determined as follows:

1) by determination of the difference of the protein content in each case, by means of the BRADFORD Test and the enzymatic activity which was present in the starting solution and finally in the remaining solution, 2) by determination of the enzymatic activity of the enzyme immobilized on the ADH-PC carrier beads, for example, using the ninhydrine method. The proportion of enzyme bound to the carrier was eluted after incubation, with sodium carbonate buffer with a pH of 10.5. After pH equalization is carried out, the activity of the eluted enzyme, for example the CPA, is determined.

The determination of enzyme activity is appropriate in all cases where antibodies are present which do not detrimentally affect the enzyme activity. It turns out that the oxidatively modified antibodies which are fixed on ADH-PC carrier beads retain their full immunological activity to bind the enzyme, for example CPA.

As a reference for the molar ratio of monoclonal antibody to CPA which was observed, the value of 2:1 is stated.

As already explained, the teaching according to the invention extends to specific conjugates of antibodies containing oligosaccharides in the most general sense. Monoclonal antibodies which are aimed against antigens of the following types, for example, should be especially mentioned:

| Antigen Class | Antigen |
| --- | --- |
| Bacterial | tetanus toxoid |
| | H. influenza Type b polysaccharide |
| | diphtheria toxin |
| | *Chlamydia trachomatis* |
| | *M. Laprae* |
| | lipopolysaccharide/endotoxin |
| | pneumococci |
| | LPS of *P. aeruginosa* |
| | exotoxin of *P. aeruginosa* |
| | streptococci Group A carbohydrate |
| Viral | X31 influenza virus nucleoprotein |
| | measles virus |
| | HSV glycoprotein D |
| | measles virus nucleocapside |
| | cytomegalus virus |
| | influenza A viruses |
| | German measles virus antigens |
| | HTLV I |
| | *varicella zoster* |
| | HVsAg |
| Autoimmune | double-strand DNA |
| | islet cells (diabetes mellitus) |
| | myasthenia gravis, anti-idiotypes |
| | thyreotropin receptor |
| | rheuma factor |
| | acetyl choline receptor |
| | thyroid |
| | sperm |
| Tumor | mamma carcinoma |
| | prostate carcinoma |
| | lung carcinoma |
| | stomach carcinoma |
| | melanoma |
| | GD2 (human melanoma) |
| | glioma |
| | rectum carcinoma |
| | leukemia |
| | cervix carcinoma |
| Tissue/Blood | Rhesus D |
| | blood group antigen A |
| | HLA-A,B,C,DR |
| | intermediary filaments |
| Others | malaria |
| | Forssman antigen |
| | sheep erythrocytes |
| | nitrophenol |
| | dinitrophenol |
| | trinitrophenol |
| | keyhole-limpet hemocyanin (KLH) |
| | rheuma factor |
| | insulin |

The fixation according to the invention offers a number of advantages as compared with the state of the art.

Advantageous effects

A comparison with parallel experiments with the same antibodies under the conditions of the multi-stage process yielded approximately 70% antibody fixation there, with the antibodies in turn demonstrating an antigen binding capacity of 1 mol/mol.

The new, improved "single-crucible" process offers a number of advantages as compared with the multi-stage processes of the state of the art:

1) The need to separate the antibody from the excess periodate present after the oxidation step is eliminated; therefore, no antibodies are lost during the course of the purification step.

2) The need to destroy excess periodate by the action of chemicals is eliminated.

3) The total reaction proceeds significantly more rapidly; now, 30-60 minutes are needed until completion, as compared with 4 to 5 hours for the conventional process.

4) As a result of the decreased reaction period, the risk that the antibodies will suffer damage due to extended periodate action is reduced.

5) The reaction can be carried out with minimal amounts of antibodies and carrier material.

Obviously, numerous modifications and variations of the present invention are possible in light of the above teachings. It is therefore to be understood that within the scope of the appended claims, the invention may be practiced otherwise than as specifically described herein.

What Is New and Desired To Be Secured by Letters Patent Of The United States Is:

1. A process for the immobilization of antibodies by a single-crucible reaction comprising: reacting a purified antibody with a buffered periodate solution in an amount sufficient to produce aldehyde groups in the antibody, said reaction being done in the presence of a polymer carrier material which has been modified with adipic acid dihydrazide.

2. The process of claim 1 wherein the time allowed for oxidation and coupling is approximately 30-60 minutes.

3. A process for the immobilization of antibodies by a single-crucible reaction comprising:
reacting a purified antibody with 0.01-1.0 molar periodate solution in a buffer of pH 3.0-7.0 thereby producing aldehyde groups in the antibody; in the presence of a copolymer of acrylamide or methacrylamide and glycidyl acrylate or glycidyl methacrylate which has been modified with adipic acid dihydrazide, for a time sufficient to couple said antibodies to said modified copolymer at a temperature between about 0°-5° C.

4. The process of claim 3 wherein the time allowed for oxidation and coupling is approximately 30-60 minutes.

5. The process of claim 4 wherein the buffer is at approximately pH 5.5.

6. The process of claim 3 wherein the buffer is 0.1 molar acetate buffer.

7. The process of claim 3 wherein the temperature is approximately 4° C.

8. The process of claim 3 wherein the copolymer has an epoxide content of 800-1000 mmol/g before modification with adipic acid dihydrazide.

* * * * *